US012685729B2

(12) United States Patent
Yoon et al.

(10) Patent No.: US 12,685,729 B2
(45) Date of Patent: Jul. 21, 2026

(54) USE OF 2,3,5-SUBSTITUTED THIOPHENE COMPOUND FOR ENHANCEMENT OF RADIOTHERAPY

(71) Applicant: Pharos iBio Co., Ltd., Anyang-si (KR)

(72) Inventors: Jeong Hyeok Yoon, Yongin-Si (KR); Ky Youb Nam, Goyang-Si (KR)

(73) Assignee: PHAROS IBIO CO., LTD., Gyeonggi-Do (KR)

( * ) Notice: Subject to any disclaimer, the term of this patent is extended or adjusted under 35 U.S.C. 154(b) by 738 days.

(21) Appl. No.: 17/059,025

(22) PCT Filed: May 29, 2019

(86) PCT No.: PCT/KR2019/006406
§ 371 (c)(1),
(2) Date: Nov. 25, 2020

(87) PCT Pub. No.: WO2019/231221
PCT Pub. Date: Dec. 5, 2019

(65) Prior Publication Data

US 2021/0205289 A1 Jul. 8, 2021

(30) Foreign Application Priority Data

May 30, 2018 (KR) ........................ 10-2018-0061790

(51) Int. Cl.
*A61K 31/4535* (2006.01)
*A61K 41/00* (2020.01)
*A61P 35/00* (2006.01)

(52) U.S. Cl.
CPC .......... *A61K 31/4535* (2013.01); *A61K 41/00* (2013.01); *A61P 35/00* (2018.01)

(58) Field of Classification Search
CPC ...... A61K 31/4535; A61K 41/00; A61P 35/00
See application file for complete search history.

(56) References Cited

U.S. PATENT DOCUMENTS

| | | | | |
|---|---|---|---|---|
| 9,655,965 | B2 * | 5/2017 | Lu | A61K 41/0038 |
| 2011/0250292 | A1 * | 10/2011 | Bae | A61P 35/00 423/617 |

FOREIGN PATENT DOCUMENTS

| | | | | | |
|---|---|---|---|---|---|
| EP | 3418275 | A1 | 12/2018 | | |
| KR | 1020030071029 | A | 9/2003 | | |
| KR | 1020030095188 | A | 12/2003 | | |
| KR | 1020060127127 | A | 12/2006 | | |
| KR | 101700599 | B1 | 1/2017 | | |
| KR | 1020170096599 | A | 8/2017 | | |
| WO | WO-2017142325 | A1 * | 8/2017 | | A61K 31/381 |

OTHER PUBLICATIONS

WO-2017142325-A1. Tae Bo Sim, et al; Translation of the '325 publication. (Year: 2017).*

Sharma, R., Plummer, R., Stock, J. et al. Clinical development of new drug-radiotherapy combinations. Nat Rev Clin Oncol 13, 627-642 (2016). (Year: 2016).*

PatentScope WO-2017142325-A1. Tae Bo Sim, et al; Translation of the '325 publication. (Year: 2017).*

National Center for Biotechnology Information (2024). PubChem Compound Summary for CID 130358571, U2UY9Tbq8Z. Retrieved Sep. 27, 2024 from https://pubchem.ncbi.nlm.nih.go (Year: 2017).*

Extended European Search Report corresponding to EP 19812646.8 mailed Feb. 25, 2022 (9 pages).

Qiu, Zhaojun, et al., "ATR/CHK1 inhibitors and cancer therapy", Radiotherapy and Oncology. 126:450-464 (2018).

Mitsuhashi. "Chemoradiation therapy" The medical frontline, 64(6):1129-1136 (2009).

Cowen, Rachel L., et al., "Hypoxia Targeted Gene Therapy to Increase the Efficacy of Tirapazamine as an Adjuvant to Radiotherapy: Reversing Tumor Radioresistance and Effecting Cure", Cancer Research 64:1396-1402, 2004.

* cited by examiner

*Primary Examiner* — Po-Chih Chen
(74) *Attorney, Agent, or Firm* — Wenderoth, Lind & Ponack, L.L.P.

(57) ABSTRACT

The present disclosure relates to a composition for enhancing radiotherapy, the composition containing a 2,3,5-substituted thiophene compound of Formula 1 or a pharmaceutically acceptable salt thereof. The composition may increase the sensitivity of cancer cells to radiation, and thus may be advantageously used to enhance the effect of radiotherapy. Also provided is a method for anticancer radiotherapy, the method including steps of: administering the composition for enhancing radiotherapy to a subject; and irradiating the subject with radiation. Further provided is a method for enhancing the effect of radiotherapy, the method including a step of administering the composition for enhancing radiotherapy to a subject.

6 Claims, 4 Drawing Sheets

USE OF 2,3,5-SUBSTITUTED THIOPHENE COMPOUND FOR ENHANCEMENT OF RADIOTHERAPY

The present disclosure was made with the support of the Korean government under grant number HI17C-2314-010017 ("Non-Clinical Study of New Candidate Compounds for Targeted Treatment of Acute Myelogenous Leukemia") awarded by the Ministry of Health and Welfare.

The present disclosure was made with the support of the Korean government under grant number S2531389 ("Global Development of Anticancer Drug of Second-Generation FLT3 Inhibitor PHI-101") awarded by the Small and Medium Business Administration.

TECHNICAL FIELD

The present disclosure relates to a use for enhancing radiotherapy.

BACKGROUND ART

With the development of modern medicine, many diseases have been treated and prevented, but cancer is still one of diseases difficult to treat. Currently, cancer is the first leading cause of death and continues to increase.

As a method for treating cancer, chemotherapy, surgical therapy and/or radiotherapy, etc. are used. The number of cancer patients receiving radiotherapy is increasing every year, and the importance of low-cost and effective radiotherapy in cancer treatment is also increasing. However, acquisition of resistance of cancer cells to radiation, damage to normal tissues during high-dose radiotherapy, and the like have been pointed out as problems of reducing the efficiency of radiotherapy. Thus, studies on radiotherapy sensitizers for enhancing the efficiency of radiotherapy have been attempted. Radiotherapy sensitizers reported to date include tirapazamine that has no properties as an anticancer drug and is used only to enhance sensitivity to radiotherapy. However, it is known that tirapazamine is effective only against hypoxic tumor cells, and the effect thereof in clinical radiotherapy is weak because drug delivery into tumor is insufficient due to the internal pressure of the tumor, which is peculiar to the hypoxia state.

In addition, in the process of cancer treatment, the therapeutic effects of many anticancer drugs and radiotherapy are reduced by DNA damage response (DDR). It is well known that the DDR pathways are associated with cellular signaling cascades (Zuco V, Benedetti V, Zunino F. ATM- and ATR-mediated response to DNA damage induced by a novel camptothecin, ST1968. Cancer Lett. 2010; 292:186-196), which are ATM (ataxia telangiectasia mutated) and checkpoint kinase 2 (CHK2) which is a downstream signaling target. ATM plays a very important role as a DNA damage sensor in DDR and activates DNA double-strand breaks (DSBs) (Ambrose M, Gatti R A. Pathogenesis of ataxia-telangiectasia: the next generation of ATM functions. Blood. 2013; 121:4036-4045). It is known that activated ATM uses, as substrates, proteins such as various DNA repair-related histones H2AX, nibrin (Nbs1), BRCA1, cell cycle checkpoint kinases CHK1 and CHK2, and p53 (Shiloh Y, Ziv Y. The ATM protein kinase: regulating the cellular response to genotoxic stress, and more. Nat Rev Mol Cell Biol. 2013; 14:197-210). It is known that the most: important substrate for ATM is the CHK2 protein (Takemura H, Rao V A, Sordet O, Furuta T, Miao Z H, Meng L, et al. Defective Mre11-dependent activation of CHK2 by ATM in colorectal carcinoma cells in response to replication-dependent DNA DSBs. J Biol Chem. 2006; 281:30814-30823), and the CHK2 protein plays two roles: apoptosis, and activation of cell cycle checkpoints (Antoni L, Sodha N, Collins I, Garrett M D. CHK2 kinase: cancer susceptibility and cancer therapy-two sides of the same coin? Nat rev Cancer. 2007; 7:925-936, and McGowan C H. CHK2: a tumor suppressor or not? Cell Cycle. 2002; 1:401-403). It is known that the CHK2 protein plays an important role in cell cycle arrest in the DSB process (Bartek J, Lukas J. CHK1 and CHK2 kinases in checkpoint control and cancer. Cancer Cell. 2003; 3:421-429; Pommier Y, Weinstein J N, Aladjem M I, Kohn K W. CHK2 molecular interaction map and rationale for CHK2 inhibitors. Clin Cancer Res. 2006; 12: 2657-2661), and another CHK1 protein has a role in the process of repair of single-stranded DNA (ssDNA) by activation of the ATR protein (Nam E A, Cortez D. ATR signalling: more than meeting at the fork. Biochem J. 2011; 436:527-536). Therefore, it is possible to increase the sensitivity of cancer cells to radiation by inhibiting the DNA damage repair (DDR) process by radiation.

Accordingly, the present inventors have conducted studies on a novel method for enhancing radiotherapy, thereby completing the present disclosure.

DISCLOSURE

Technical Problem

An object of the present disclosure is to provide a composition for enhancing radiotherapy, the composition containing a compound represented by Formula 1 below or a pharmaceutically acceptable salt thereof.

Another object of the present disclosure is to provide a method for anticancer radiotherapy, the method including steps of: administering the composition for enhancing radiotherapy to a subject; and irradiating the subject with radiation.

Still another object of the present disclosure is to provide a method for enhancing the effect of radiotherapy, the method including a step of administering the composition for enhancing radiotherapy to a subject.

[Formula 1]

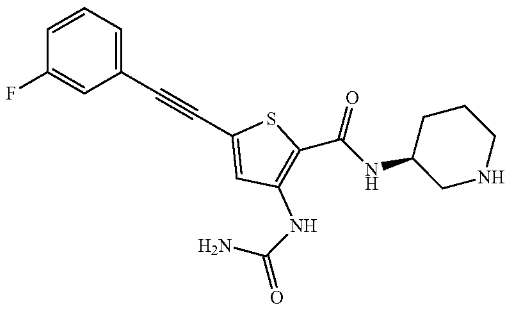

Technical Solution

One aspect of the present disclosure provides a composition for enhancing radiotherapy against cancer, the composition containing a compound represented by the following Formula 1 or a pharmaceutically acceptable salt thereof:

[Formula 1]

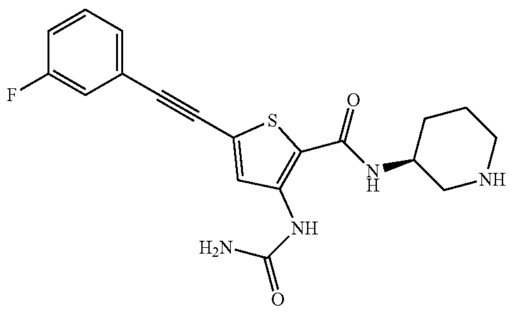

According to one embodiment of the present disclosure, the cancer may be colorectal cancer, head and neck cancer or breast cancer.

According to one embodiment of the present disclosure, the pharmaceutically acceptable salt may be a hydrochloride salt.

According to one embodiment of the present disclosure, the composition may be administered before irradiation, after irradiation, or simultaneously with irradiation.

Another aspect of the present disclosure provides a method for anticancer radiotherapy, the method including steps of: administering the composition for enhancing radiotherapy to a subject; and irradiating the subject with radiation.

According to one embodiment of the present disclosure, the step of administering may be performed before irradiation, after irradiation, or simultaneously with irradiation.

Still another aspect of the present disclosure provides a method for enhancing the effect of radiotherapy, the method including a step of administering the composition for enhancing radiotherapy to a subject.

Advantageous Effects

The composition for enhancing radiotherapy according to one embodiment of the present disclosure may increase the radiation sensitivity of cancer cells, and thus may be advantageously used to enhance the effect of radiotherapy.

BEST MODE

Figure 1:
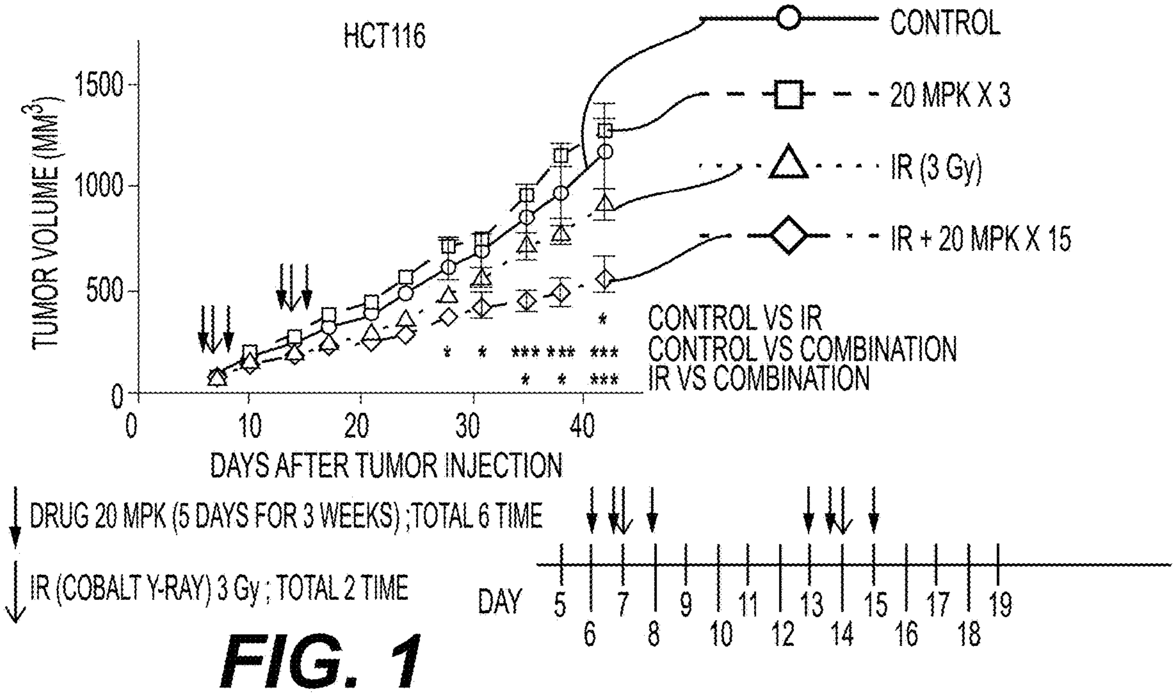
FIG. 1 is a graph showing the change in tumor volume after a composition (20 mg/kg: 20 mpk) for enhancing radiotherapy according to one embodiment of the present disclosure was administered to mice 7 days after transplantation with the HCT116 colorectal cancer cell line, 24 hours and 3 hours before and 24 hours after treatment with radiation (3 Gy), or without treatment with radiation. Administration of the composition for enhancing radiotherapy according to one embodiment of the present disclosure and treatment with radiation were repeated twice at 7-day intervals.

One aspect of the present disclosure provides a composition for enhancing radiotherapy against cancer, the composition containing a compound represented by the following Formula 1 or a pharmaceutically acceptable salt thereof:

[Formula 1]

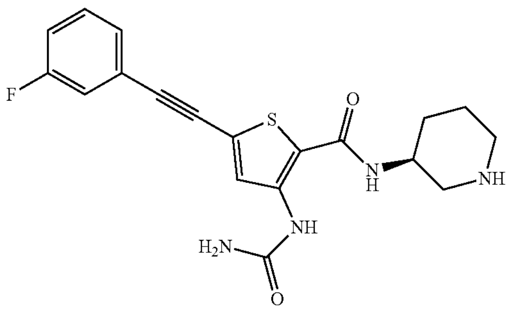

The compound represented by Formula 1, which is contained as an active ingredient in the composition for enhancing radiotherapy according to the present disclosure, is (S)-5-((3-fluorophenyl) ethynyl)-N-(piperidin-3-yl)-3-ureido-thiophene-2-carboxamide. The compound represented by Formula 1 may increase the radiation sensitivity of cancer cells, and thus may act as a radiotherapy enhancer.

As used herein, the term "radiotherapy enhancer" is also referred to as "radiation sensitizer", and refers to an agent that is used in combination with anticancer radiotherapy to increase the sensitivity of cancer cells to radiation, thus enhancing the efficiency of radiotherapy. For example, when radiotherapy and the radiation sensitizer are used in combination in cancer treatment, the sensitivity of cancer cells to radiation may be increased, and thus the effects of killing the cancer cells and inhibiting the proliferation of the cancer cells may increase. In addition, the radiotherapy enhancer may exhibit an excellent anticancer effect even at a lower dose than a common radiation dose that is used in radiotherapy, and thus the adverse effects of radiotherapy, such as acquisition of radiation resistance and damage to normal tissue in high-dose radiotherapy, may be reduced. Therefore, the radiotherapy enhancer may be advantageously used not only for cancer treatment, but also for the prevention of cancer metastasis and/or cancer recurrence.

The composition for enhancing radiotherapy according to the present disclosure may exhibit anticancer activity even by itself, and may increase the sensitivity of cancer cells to radiation. Therefore, the composition for enhancing radiotherapy according to the present disclosure may be administered before and/or after irradiation to significantly enhance the effect of radiotherapy by a synergistic effect.

According to one embodiment of the present disclosure, the cancer may be a cancer selected from the group consisting of stomach cancer, lung cancer, liver cancer, colorectal cancer, small intestine cancer, pancreatic cancer, brain cancer, breast cancer, uterine cancer, cervical cancer, head and neck cancer, esophageal cancer, thyroid cancer, parathyroid cancer, kidney cancer, prostate cancer, urethral cancer and bladder cancer.

According to one embodiment of the present disclosure, the cancer may be colorectal cancer, head and neck cancer, or breast cancer.

In the present disclosure, it was confirmed through in vivo data that, when the composition for enhancing radiotherapy according to the present disclosure was used in combination with irradiation, the effects of inhibiting the proliferation of cancer cells in the breast cancer cell lines BT549 and JIMT-1, the colorectal cancer cell lines HT29 and HCT116 and the head and neck cancer cell line FaDu and thus inhibiting tumor proliferation increased compared to when irradiation was used alone. Therefore, the composition for enhancing radiotherapy according to the present disclosure may be advantageously used as a radiation sensitizer in radiotherapy for cancers such as colorectal cancer, head and neck cancer, and breast cancer.

As used herein, the term “irradiation” refers to local treatment methods that damage DNA of malignant cells, and includes general irradiation methods that are used for the treatment of cancer. The irradiation methods include, for example, but are not limited to, deep X-ray therapy, radium therapy, high-dose irradiation with cobalt 60, ultra-high pressure radiotherapy, and radioisotope therapy. The dose of radiation may be at a low level of 2 Gy to 100 Gy.

A pharmaceutically acceptable salt of the compound represented by Formula 1 may be appropriately produced or selected by using known knowledge by a person skilled in the art. For example, the pharmaceutically acceptable salt that is contained in the composition for enhancing radiotherapy according to the present disclosure may be a salt having safety and efficacy profiles suitable for administration to humans. Specifically, pharmaceutically acceptable salts of the compound represented by Formula 1 include, but are not limited to, salts derived from inorganic acids, for example, hydrochloric acid, nitric acid, phosphoric acid, sulfuric acid, hydrobromic acid, hydroiodic acid, phosphorous acid, and mixtures thereof, as well as salts derived from organic acids, for example, aliphatic mono- and dicarboxylic acids, phenyl-substituted alkanoic acids, hydroxyalkanoic acids, alkanedioic acids, aromatic acids, and aliphatic and aromatic sulfonic acids.

The composition for enhancing radiotherapy according to one embodiment of the present disclosure may be administered together with one or more known radiation sensitizers.

The composition for enhancing radiotherapy according to the present disclosure is administered in radiotherapy, and may be administered before and/or after radiotherapy. The dose of the composition may vary depending on factors such as the content of the active ingredient in the composition, the severity of the disease, the weight of the patient, the form of the drug, the route of administration, and the duration of administration. The dose of the composition for enhancing radiotherapy according to the present disclosure may be 0.1 to 500 mg/kg for an adult, and may be administered once a day or administered about 2 to 4 times a day.

According to one embodiment of the present disclosure, the composition may be administered before irradiation, after irradiation or simultaneously with irradiation.

According to one embodiment of the present disclosure, the composition for enhancing radiotherapy according to the present disclosure may be administered 24 hours to 3 hours before irradiation, for example, 20 hours, 18 hours, 12 hours, 8 hours, 6 hours or 3 hours before irradiation, and 3 to 96 hours after irradiation, for example, 96 hours, 72 hours, 48 hours, 24 hours, 20 hours, 18 hours, 12 hours, 8 hours, 6 hours or 3 hours after irradiation.

According to one embodiment of the present disclosure, the composition may be formulated as an oral formulation or an injectable formulation.

The composition for enhancing radiotherapy according to the present disclosure may be administered orally or parenterally. For example, the radiotherapy enhancer of the present disclosure may be formulated as oral formulations such as granules, powders, solutions, tablets, capsules or dry syrups, or as parenteral formulations such as an injectable formulation, and administered orally or parenterally.

The composition for enhancing radiotherapy according to the present disclosure may contain various bases and/or additives that are necessary and appropriate for formulation thereof. In addition, the composition may be prepared to further contain known compounds such as a nonionic surfactant, a silicone polymer, an extender pigment, fragrance, a preservative, a disinfectant, an oxidation stabilizer, an organic solvent, an ionic or nonionic thickener, a softening agent, an antioxidant, a free radical destroying agent, an opacifying agent, a stabilizer, an emollient, silicone, $\alpha$-hydroxyl acid, an antifoaming agent, a moisturizer, vitamins, an insect repellent, fragrance, a preservative, a surfactant, an anti-inflammatory agent, a substance P antagonist, a filler, a polymer, a propellant, a basifying or acidifying agent, or a colorant, within a range that does not impair the effects thereof.

The composition for enhancing radiotherapy according to the present disclosure may contain a pharmaceutically acceptable carrier. The pharmaceutically acceptable carrier that is contained in the composition for enhancing radiotherapy according to the present disclosure may be a carrier or diluent that does not stimulate an organism and does not inhibit the biological activity and properties of the compound administered. As a pharmaceutically acceptable carrier for the composition which is formulated as a liquid solution, there may be used one or more of saline, sterile water, Ringer’s solution, buffered saline, albumin solution for injection, dextrose solution, maltodextrin solution, glycerol, ethanol, and a mixture of two or more of these components, which are sterilized and biocompatible. In addition, the composition may, if necessary, contain other conventional additives such as antioxidants, buffers and bacteriostatic agents. In addition, the carriers may include non-naturally occurring carriers. In preparation of the composition for enhancing radiotherapy according to the present disclosure, an appropriate carrier may be selected depending on the formulation to be prepared, and the composition may be formulated by mixing the selected carrier with the compound represented by Formula 1 as an active ingredient at an appropriate ratio.

According to one embodiment of the present disclosure, the pharmaceutically acceptable salt may be a hydrochloride salt.

Another aspect of the present disclosure provides a method for anticancer radiotherapy, the method including steps of: administering the composition for enhancing radiotherapy to a subject; and irradiating the subject with radiation.

According to one embodiment of the present disclosure, the step of administering may be performed before irradiation, after irradiation, or simultaneously with irradiation.

The step of administering the composition for enhancing radiotherapy to a subject may be performed 24 hours to 3 hours before irradiation, for example, 20 hours, 18 hours, 12 hours, 8 hours, 6 hours or 3 hours before irradiation, and 3 hours to 96 hours after irradiation, for example, 96 hours, 72 hours, 48 hours, 24 hours, 20 hours, 18 hours, 12 hours, 8 hours, 6 hours or 3 hours after irradiation.

The anticancer radiotherapy may be performed by various known irradiation methods, including, but not limited to, deep X-ray therapy, radium therapy, high-dose irradiation with cobalt 60, ultra-high pressure radiotherapy, and radioisotope therapy.

The anticancer radiotherapy may be performed with low-dose radiation of 2 Gy to 100 Gy for 1 to 30 minutes. When the anticancer radiotherapy is performed within the above dose range, it is possible to minimize the adverse effects of radiation and, at the same time, maximize the anticancer treatment effects of the composition for enhancing radiotherapy according to one embodiment of the present disclosure and radiation.

Still another aspect of the present disclosure provides a method for enhancing the effect of radiotherapy, the method including a step of administering the composition for enhancing radiotherapy to a subject.

In the method for enhancing the effect of radiotherapy, the timing of administration of the composition for enhancing radiotherapy and the radiotherapy method are the same as described above.

MODE FOR INVENTION

Hereafter, the present disclosure will be described in more detail with reference to one or more examples. However, these examples are to describe the present disclosure by way of example, and the scope of the present disclosure is not limited to these examples.

Example 1. Animal Model Preparation 1-1. Mouse Preparation 6-week-old female Balb/c nu/nu mice (Orient Bio Inc.) and NOD SCID mice (Orient Bio Inc.) were prepared. The mice were acclimated for 1 week after purchase, and then tumor transplants were prepared. During the animal experiment, cages were replaced once a week, and drinking water and feed were often checked to ensure that they were always sufficiently supplied.

1-2. Tumor Cell Preparation and Transplantation

Each of the tumor cell lines shown in Table 1 below was cultured with DMEM (Dulbecco's Modified Eagle Medium) or RPMI-1640 in a 150-mm culture dish (SPL) under 5% $CO_2$ at 37° C. Then, each tumor cell line was diluted to a density of $1\times10^6$ cells/100 μl using cold DPBS buffer (Welgene), and kept cold on ice until transplantation.

TABLE 1

| Cell line | Kind of cancer | Source | Cat # |
|---|---|---|---|
| HCT116 | Colorectal cancer | ATCC | CCL-247 |
| JIMT-1 | Breast cancer | ATCC | CVCL-2077 |
| FaDu | Head and neck cancer | ATCC | HTB-43 |

Thereafter, the tumor cells were transplanted into the mice by subcutaneous injection of 100 μl of the prepared tumor cell dilution into the right thigh of each of the mice prepared in Example 1-1.

1-3. Preparation of Mouse Model Transplanted with Tumor Cells

When each tumor cell line transplanted to the mice in Example 1-2 proliferated and the tumor begun to be visible, the lengths of the longest and shortest diameters of the tumor were measured using digital calipers (Mitutoyo). When the average volume of the tumor reached about 100 to 150 $mm^3$, the mice were divided into a plurality of groups, each consisting of 4 to 6 mice, according to the '‘ㄹ’' method in order to start drug administration and irradiation, and mice having an excessively large or small tumor volume were excluded.

Example 2. Measurement of Tumor Volume in Animal Model after Drug and/or Radiation Treatment 2-1. Measurement of Tumor Volume in Animal Model 2-1-1. Drug Preparation A hydrochloride salt of the compound represented by Formula 1 (hereinafter referred to as 'PHI-101'), which was prepared at a concentration of 200 mM in DMSO (Sigma), was diluted in 20% 2-hydroxypropyl-β-cyclodextrin (Sigma) in DPBS, and a control was prepared by diluting DMSO to the same concentration. The volume administered was basically set to 100 μl. However, when the dose was 80 mg/kg and the compound was diluted to 100 μl, the concentration of DMSO became 10% or more, and thus in this case, the volume administered was 200 μl.

[Formula 1]

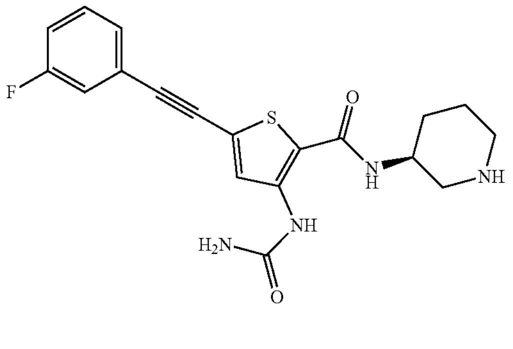

2-1-2. Radiation Treatment

For irradiation, mice were anesthetized by intraperitoneally injecting a mixture of zoletil 50 (Virbac) and rompun (Bayer) according to the instruction manual at a volume of 100 μl per mouse. Each of the anesthetized mice was fixed to a plate for irradiation by a tape so that only the tumor site could be irradiated with radiation.

Irradiation was performed using an X-RAD 320 irradiator (Pxi Precision X-Ray) and a $^{60}$Co γ-ray irradiator. To evaluate the effect of a combination of the drug and radiotherapy, the intensity of radiation and the number of times of irradiation were adjusted according to the characteristics of the cell line so that the anticancer effect of radiation alone did not strongly appear.

Specifically, the mice were irradiated with X-rays with an intensity of 2 Gy per minute once or several times within the range of 1 to 5 Gy. The field size for X-ray irradiation was set to 20×5 cm, and the field size for $^{60}$Co γ-ray irradiation was set to 30×3 cm, so that only the leg portion transplanted with the tumor was exposed to radiation.

2-1-3. Tumor Volume Analysis

The tumor volume was measured at intervals of 2 to 4 days, and was calculated using the following equation:

$$V=\frac{1}{2}(L\times W^2)$$

V=volume (mm$^3$)

L=length [mm], the longest diameter

W=width [mm], the shortest diameter

The measurement end time was determined based on when the average volume of the control tumor reached about 2,000 mm$^3$. The data of the measured tumor volume was first organized in Microsoft Excel, and plotted in GraphPad Prism. Statistical significance was analyzed using two-way ANOVA in GraphPad Prism.

2-2. Evaluation of Effect on Reduction in Tumor Volume of Tumor Cell Line Transplanted into Mice 2-2-1. Evaluation of Effect on Reduction in Tumor Volume of HCT116 Cell Line Evaluation was made as to whether the PHI-101 compound can act as a radiotherapy sensitizer for colorectal cancer.

Specifically, the drug prepared in Example 2-1-2 was administered intraperitoneally at a dose of 20 mg/kg to each of the mice transplanted with the HCT116 cell line according to Example 1-3, 24 hours and 3 hours before and 24 hours after the mice were irradiated with radiation of 3 Gy using an X-RAD 320 irradiator according to the method of Example 2-1-2. The drug administration and the irradiation were repeated twice at an interval of one week. Then, the tumor volume was analyzed according to the method of Example 2-1-3.

As a result, it was confirmed that, when administration of the PHI-101 compound and radiation were performed in combination, in the case of the group to which the drug was administered three times a week at a dose of 20 mg/kg, the tumor volume was reduced by 49.58% compared to that in the control group, and the tumor volume was inhibited by 36.60% compared to when only irradiation was performed (FIG. 1).

2-2-2. Evaluation of Effect on Reduction in Tumor Volume of JIMT-1 Cell Line

Evaluation was made as to whether the PHI-101 compound can act as a radiotherapy sensitizer for breast cancer.

Specifically, the drug prepared in Example 2-1-2 was administered intraperitoneally at a dose of 20 mg/kg to each of the mice transplanted with the JIMT-1 cell line according to Example 1-3, 24 hours and 3 hours before and 24 hours, 48 hours and 72 hours after the mice were irradiated with radiation of 3 Gy using a 60Co γ-ray irradiator according to the method of Example 2-1-2. The drug administration and the irradiation were repeated three times for 3 weeks. Then, the tumor volume was analyzed according to the method of Example 2-1-3.

Figure 2:
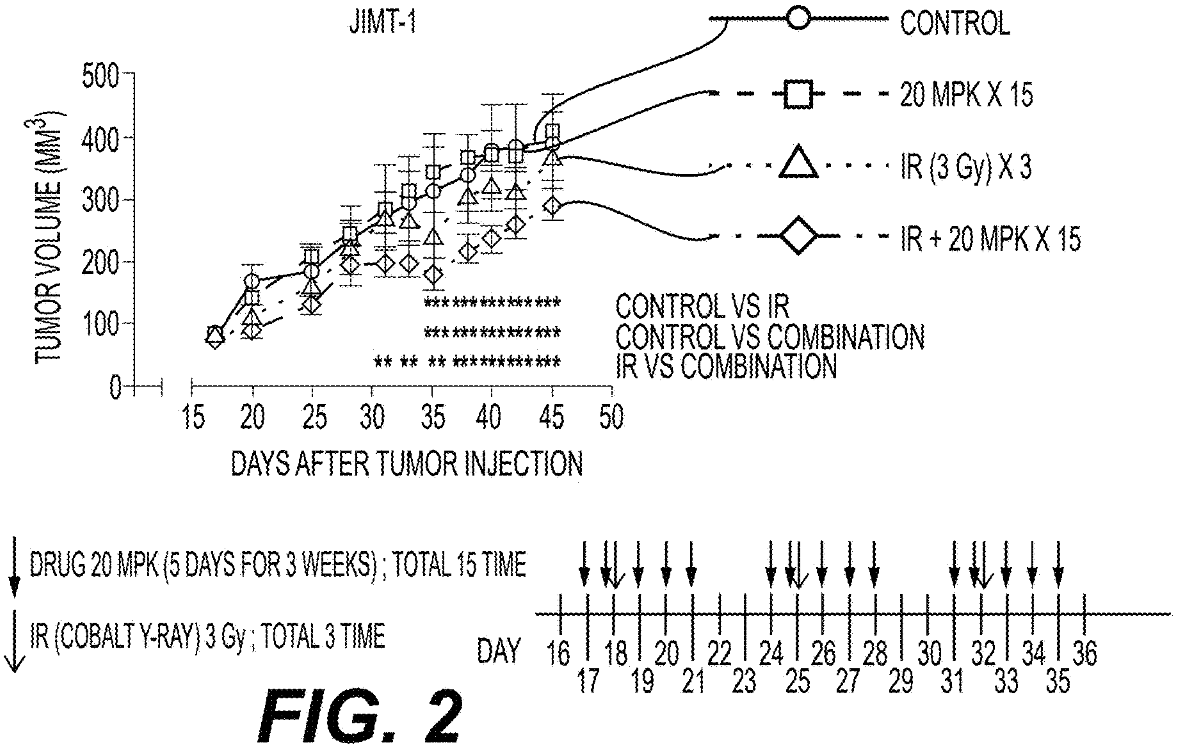
FIG. 2 is a graph showing the change in tumor volume after a composition (20 mg/kg: 20 mpk) for enhancing radiotherapy according to one embodiment of the present disclosure was administered to mice 7 days after transplantation with the JIMT-1 breast cancer cell line, 24 hours and 3 hours before and 24 hours, 48 hours and 72 hours after treatment with radiation (3 Gy), or without treatment with radiation. Administration of the composition for enhancing radiotherapy according to one embodiment of the present disclosure and treatment with radiation were repeated three times at 7-day intervals.

As a result, it was confirmed that, when administration of the PHI-101 compound and irradiation were performed in combination, the tumor volume was reduced by 27.32% compared to that in the control group, and the tumor volume was inhibited by 20.53% compared to when only irradiation was performed (FIG. 2).

2-2-3. Evaluation of Effect on Reduction in Tumor Volume of FaDu Cell Line

Evaluation was made as to whether the PHI-101 compound can act as a radiotherapy sensitizer for head and neck cancer.

Specifically, the drug prepared in Example 2-1-2 was administered intraperitoneally at a dose of 20 mg/kg to each of the mice transplanted with the FaDu cell line according to Example 1-3, 3 hours before and 24 hours, 48 hours, 72 hours and 96 hours after the mice were irradiated with radiation of 3 Gy using a $^{60}$Co γ-ray irradiator according to the method of Example 2-1-2. The drug administration and the irradiation were repeated three times for 3 weeks. Then, the tumor volume was analyzed according to the method of Example 2-1-3.

Figure 3:
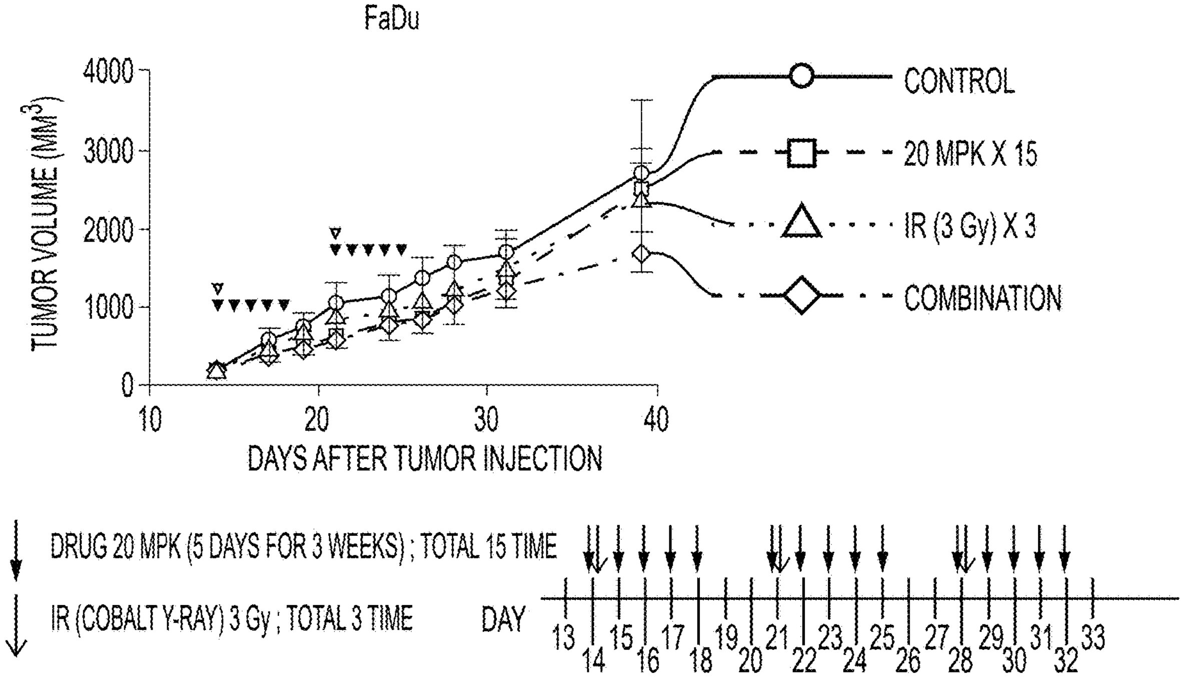
FIG. 3 is a graph showing the change in tumor volume after a composition (20 mg/kg: 20 mpk) for enhancing radiotherapy according to one embodiment of the present disclosure was administered to mice 7 days after transplantation with the FaDu head and neck cancer cell line, 3 hours before and 24 hours, 48 hours, 72 hours and 96 hours after treatment with radiation (3 Gy), or without treatment with radiation. Administration of the composition for enhancing radiotherapy according to one embodiment of the present disclosure and treatment with radiation were repeated three times at 7-day intervals.

As a result, it was confirmed that, when administration of the PHI-101 compound and irradiation were performed in combination, the tumor volume was reduced by 37.50% compared to that in the control group, and the tumor volume was inhibited by 29.16% compared to when only irradiation was performed (FIG. 3).

Example 3. Measurement of Breast Cancer Cell Inhibitory Activity after Drug and Radiation Treatment Whether the PHI-101 compound can act as a radiotherapy sensitizer for breast cancer was evaluated using clonogenic assay.

Specifically, each of the breast cancer cell lines shown in Table 2 below was added to DMEM medium in a 60-mm dish at a density of 300 cells, and treated with PHI-101 at a concentration of 0.1, 0.2 or 0.5 μM. As a control, DMSO was used.

TABLE 2

| Cell line | Source | Cat # |
|---|---|---|
| JIMT-1 | DSMZ | ACC589 |
| MDA-MB-468 | ATCC | HTB-132 |

3 hours after PHI-101 treatment, the cells were irradiated with radiation having an intensity of 0, 1, 2 or 3 Gy. Next, the cells were cultured under 5% $CO_2$ at 37° C. for 10 days, and then the formed colonies were stained with 0.4% crystal violet. Then, the colonies were counted and the surviving fraction of the cells was calculated. The results of calculating the surviving fraction were normalized and fitted to a linear-quadratic model using Kaleidagraph version 351 (Synergy Software, Reading, PA).

Figure 4:
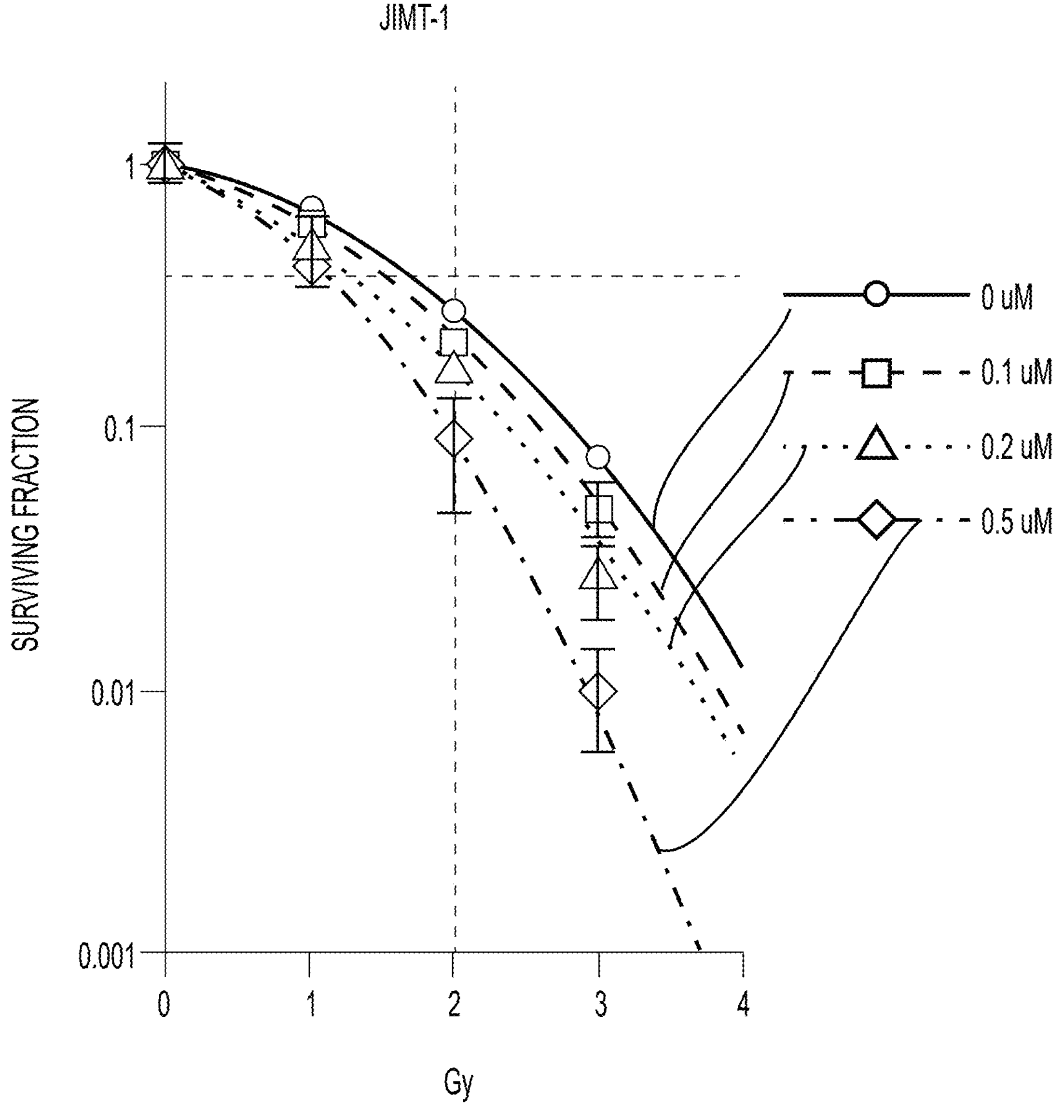
FIG. 4 is a graph showing the results obtained by treating the JIMT-1 breast cancer cell line with a composition (0.1, 0.2 or 0.5 μM) for enhancing radiotherapy according to one embodiment of the present disclosure, irradiating the cell line with radiation having an intensity of 0, 1, 2 or 3 Gy 3 hours after treatment with the composition, calculating the surviving fraction of the cells 10 days after irradiation, and fitting the surviving fraction to a linear-quadratic model.
Figure 5:
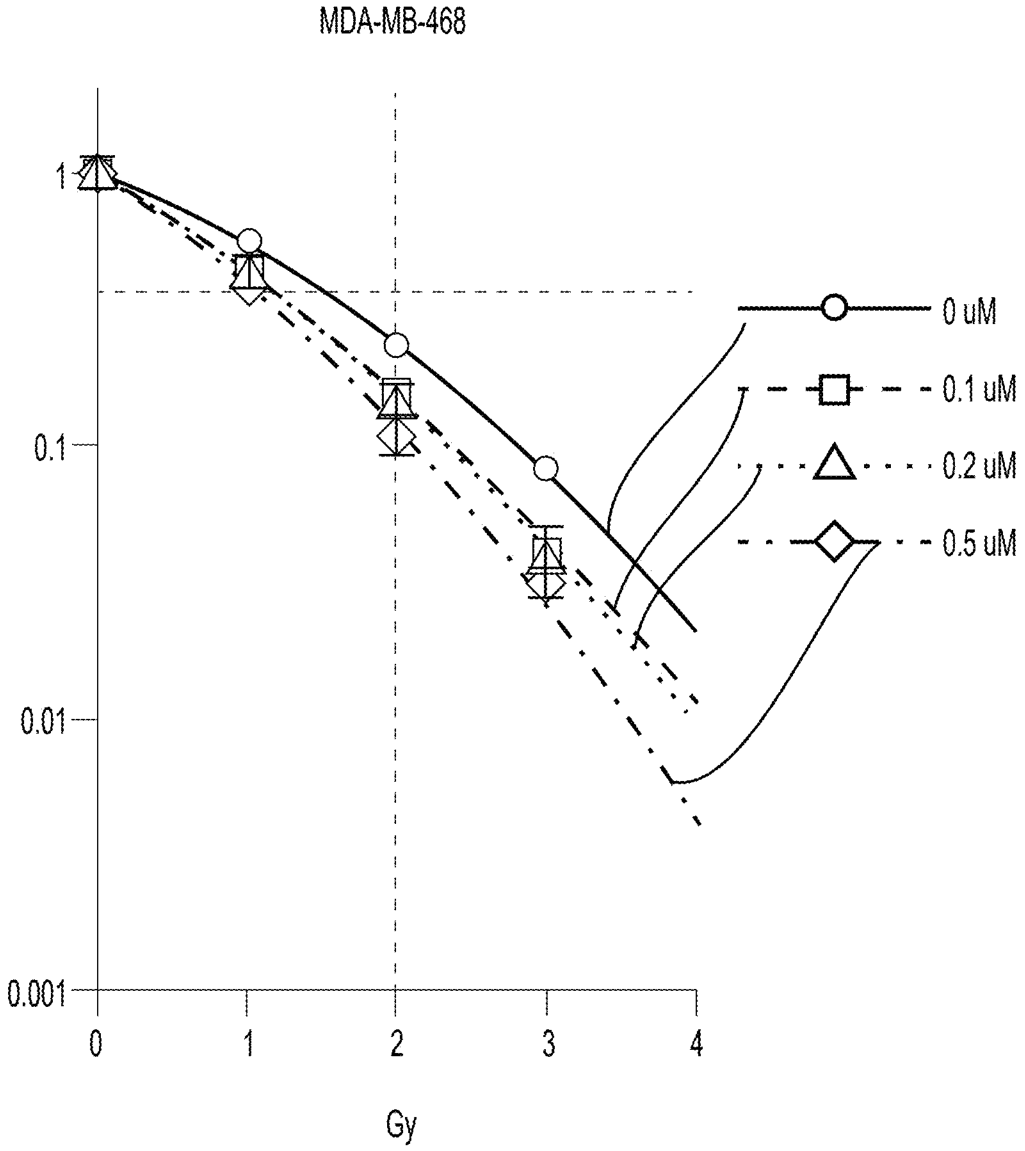
FIG. 5 is a graph showing the results obtained by treating the MDA-MB-468 breast cancer cell line with a composition (0.1, 0.2 or 0.5 μM) for enhancing radiotherapy according to one embodiment of the present disclosure, irradiating the cell line with radiation having an intensity of 0, 1, 2 or 3 Gy 3 hours after treatment with the composition, calculating the surviving fraction of the cells 10 days after irradiation, and fitting the surviving fraction to a linear-quadratic model.

As a result, it was confirmed that, when the breast cancer cells (JIMT-1 and MDA-MB-468) were treated with PHI- 101, the radiation sensitivity of the breast cancer cells increased in a concentration-dependent manner (FIGS. 4 and 5).

So far, the present disclosure has been described with reference to the embodiments. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

What is claimed is:

1. A method for enhancing anticancer radiotherapy, the method comprising steps of: administering to a subject in need thereof an effective amount of a compound represented by Formula 1 or a pharmaceutically acceptable salt thereof; and irradiating the subject with radiation at 3 Gy twice at 7-day intervals, wherein the compound is administrated in combination with the radiation;

[Formula 1]

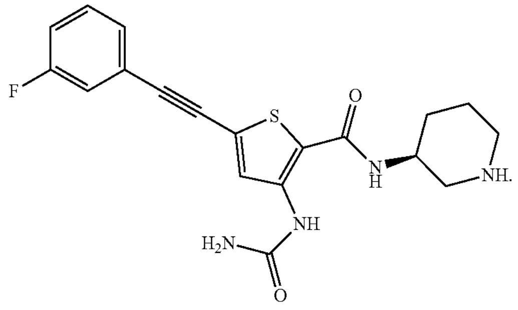

2. The method of claim 1, wherein the step of administering is performed before irradiation, after irradiation, or simultaneously with irradiation.

3. The method of claim 1, wherein the pharmaceutically acceptable salt is hydrochloride salt.

4. A method for enhancing the effect of radiotherapy, the method comprising a step of administering to a subject in need thereof an effective amount of a compound represented by Formula 1 or a pharmaceutically acceptable salt thereof, wherein the subject has cancer, and the cancer is colorectal cancer, head and neck cancer or breast cancer:

[Formula 1]

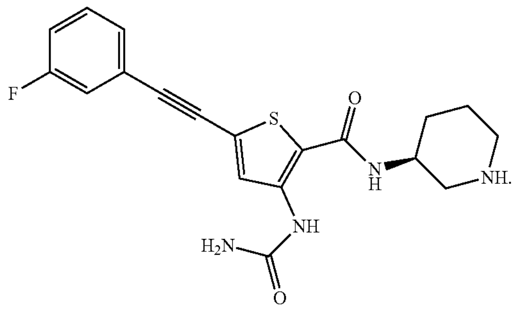

wherein the radiotherapy is irradiating the subject with radiation at 3 Gy twice at 7-day intervals, wherein the compound is administered in combination with the radiation.

5. The method of claim 4, wherein the pharmaceutically acceptable salt is hydrochloride salt.

6. The method of claim 4, wherein the compound or pharmaceutically acceptable salt thereof is administered before irradiation, after irradiation, or simultaneously with irradiation.

* * * * *